(12) United States Patent
Wu et al.

(10) Patent No.: US 8,877,682 B2
(45) Date of Patent: Nov. 4, 2014

(54) LOW USE RATE AGRICULTURAL COMPOSITIONS AND METHODS FOR USE

(75) Inventors: Dan Wu, Levittown, PA (US); Michael J. Kisenwether, Bensalem, PA (US); Krishnamurthy Shanmuganandamurthy, Plainsboro, NJ (US)

(73) Assignee: Rhodia Operations, Paris (FR)

( * ) Notice: Subject to any disclaimer, the term of this patent is extended or adjusted under 35 U.S.C. 154(b) by 837 days.

(21) Appl. No.: 12/455,403

(22) Filed: Jun. 2, 2009

(65) Prior Publication Data

US 2009/0298695 A1 Dec. 3, 2009

Related U.S. Application Data

(60) Provisional application No. 61/130,643, filed on Jun. 2, 2008, provisional application No. 61/135,561, filed on Jul. 22, 2008.

(51) Int. Cl.
 *A01N 25/10* (2006.01)
 *A01N 47/24* (2006.01)
 *A01N 53/00* (2006.01)
 *A01N 57/16* (2006.01)

(52) U.S. Cl.
 CPC ...................................... *A01N 25/10* (2013.01)
 USPC .................. 504/206; 504/362; 71/49; 71/63; 71/64.08; 514/777

(58) Field of Classification Search
 USPC ..................... 504/206, 362; 71/49, 63, 64.08; 514/777
 See application file for complete search history.

(56) References Cited

U.S. PATENT DOCUMENTS

| | | | | |
|---|---|---|---|---|
| 3,483,121 | A | 12/1969 | Jordan | 252/8.55 |
| 3,723,408 | A | 3/1973 | Nordgren et al. | 260/209 R |
| 3,723,409 | A | 3/1973 | Yueh | 260/209 R |
| 3,740,388 | A | 6/1973 | Montgomery et al. | 260/209 R |
| 4,336,145 | A * | 6/1982 | Briscoe | 507/211 |
| 4,874,854 | A * | 10/1989 | Colegrove et al. | 536/114 |
| 5,874,096 | A | 2/1999 | Hazen | 424/405 |
| 5,906,962 | A * | 5/1999 | Pallas et al. | 504/361 |
| 5,964,917 | A * | 10/1999 | Latting | 71/49 |
| 6,358,294 | B1 * | 3/2002 | Latting | 71/49 |
| 6,364,926 | B1 * | 4/2002 | Gryzik et al. | 71/64.1 |
| 2004/0211234 | A1 | 10/2004 | Volgas et al. | 71/64.1 |
| 2005/0085386 | A1 | 4/2005 | Hunter et al. | 504/116.1 |
| 2007/0054808 | A1 | 3/2007 | Brigance et al. | 504/361 |

OTHER PUBLICATIONS

Kawamura, Y., Guar Gum: Chemical and Techinical Assessment, 2008, pp. 1-4.*
AG-RHO DR 2000 Product Sheet, 2008, Rhodia, p. 1.*
Yoko, Kawamura, "Guar Gum, Chemical and Technical Assessment," 2008, 69th JECFA, pp. 1-4.*
K.L.Hodges, W.E. Kester, D.L. Wiederricb and J.A. Grover, "Determination of Alkoxyl Substitution in Cellulose Ethers by Zeisel-Gas Chromatography", Analytical Chemistry, vol. 51, No. 13, Nov. 1979.

* cited by examiner

*Primary Examiner* — Jane C Oswecki

(57) ABSTRACT

A substantially dry, flowable adjuvant compositions comprising, based on 100 parts by weight ("pbw") of the adjuvant composition: (a) from about 25 pbw to about 75 pbw of a polysaccharide and (b) from about 75 pbw to about 20 pbw of a salt composition. In one embodiment, the salt composition is diammonium hydrogen phosphate, sodium carbonate or a combination thereof, and the polysaccharide is a derivatized guar. Also disclosed are methods of preparing such agricultural compositions comprising adding, to a heel solution, (a) a water dispersible adjuvant composition, in an amount effective to provide deposition and/or drift control properties, comprising, based on 100 pbw of the adjuvant composition: (i) from about 25 pbw to about 75 pbw of a polysaccharide, and (ii) from about 75 pbw to about 20 pbw of a salt composition, wherein an aqueous solution of the adjuvant composition has a pH value of between about 7 and about 12, and (b) an effective amount of an active. The adjuvant composition can further comprise (iii) from about 20 pbw to about 30 pbw of a dispersing agent, wherein typically the dispersing agent is sodium polyacrylate.

8 Claims, No Drawings

LOW USE RATE AGRICULTURAL COMPOSITIONS AND METHODS FOR USE

CROSS-REFERENCE TO RELATED APPLICATIONS

This application claims the benefit of U.S. Provisional Application Ser. No. 61/130,643, filed Jun. 2, 2008, and U.S. Provisional Application Ser. No. 61/135,561, filed Jul. 22, 2008, herein incorporated by reference.

FIELD OF THE INVENTION

This invention relates to methods and compositions relating to agricultural compositions and, in particular, to agricultural adjuvant compositions such as pesticide compositions, fungicide compositions, herbicide compositions and the like containing high concentrations of one or more polysaccharides, and methods for using such compositions.

BACKGROUND OF THE INVENTION

Agricultural compositions including herbicides, for example, compositions containing N-(phosphonomethyl) glycine ("glyphosate") are typically applied to target plants by spraying. Spraying is typically performed from aircraft, tractors, ground rigs, irrigation systems or railcars. A portion of the spray droplets are typically very small, for example, less than about 200 microns, which are subject to off-target movement, termed "drift". Drift is undesirable because it reduces the amount of active applied to the target plant and risks unintended application of the active herbicide, pesticide, fungicide or the like to non-target plants. Further, spray droplets are subject to rebound or splashing after the droplets initially impact the target plants, which results in a reduction or loss of active ingredient on the target plants. This also raises economical and environmental concerns, as more of the spray droplets splash or rebound to the ground or on non-targeted plants.

Common approaches to reducing drift and rebound are to add one or more deposition control agents (in a concentrated liquid or dry adjuvant composition), for example, polysaccharides, polyacrylamides, to the agricultural composition. However, for such deposition control agents to properly hydrate into an aqueous solution, a relatively high amount of diammonium sulfate must also be added with the addition of the deposition control agent.

Current commercially available guar-based drift control dry adjuvant compositions comprise a large amount of salts such as diammonium sulfate. These commercially available dry adjuvant compositions generally comprise more than 85% of diammonium sulfate and less than about 10%, typically 5%, guar, by weight of the total composition. In these commercially available compositions, the high weight percentage of diammonium sulfate is important and necessary relative to the guar to ensure proper dispersion and hydration of the drift reducing agent in the aqueous tank mix. As a consequence, not more than a relatively low amount of guar (relative to the amount of diammonium sulfate) can be added to such adjuvant composition. Thus, the total amount of adjuvant composition per volume of tank mixture (i.e., the "use rate") as described above must be high in order to add an effective amount of drift control agent to the tank mixture.

As such, these formulations are commonly used with suggested high use rates (e.g., 9 lb/100 gallons), since to mix an effective amount of a drift-control agent such as guar to a tax mixture, a substantially higher amount of diammonium sulfate must be added. There are drawbacks associated with such high use rate formulation such as the costs and resources necessary for shipping and handling a large amount of material for large commercial applications, as well as the costs and resources required for storage.

It is therefore desirable to have low use rate formulations wherein a lower amount of diammonium sulfate or salt mixtures are utilized (i.e., can sufficiently hydrate the drift-control agent such as guar) relative to the guar and/or its derivatives. In some cases, however, such formulations with a proportionally higher guar to diammonium sulfate percentage cannot disperse and hydrate properly. Reference is made to high use rate formulations described in U.S. Pat. No. 6,358,294 to Latting. Insufficient dispersion of dry guar gum and/or its derivatives can result in the agglomeration and lumps of guar gel or "fish-eyes," which can lead to among other things clogging of the spray nozzles during spray application.

Accordingly, there remains a continuing interest in efficient, improved application and preparation of agricultural compositions, typically the preparation of drift and/or deposition control adjuvant composition with low use rate, ensuring proper dispersion and hydration in agricultural actives, especially glyphosate and/or glyphosate heel solutions.

SUMMARY OF INVENTION

In one aspect the present invention is a substantially dry, flowable (i.e., having the capability for flow) adjuvant composition effective at providing drift and/or deposition control properties control comprising, based on 100 parts by weight ("pbw") of the adjuvant composition: (a) from about 25 pbw to about 95 pbw of a polysaccharide and (b) from about 75 pbw to about 5 pbw of a salt composition. In one embodiment, the salt composition comprises diammonium hydrogen phosphate, sodium carbonate or a combination thereof, and the polysaccharide comprises guar gum and/or its derivatives. In one embodiment, the ratio of the polysaccharide to the salt composition is from about 25:55 parts be weight (pbw) polysaccharide:salt composition to about 55:20 pbw polysaccharide:salt composition.

Adjuvant compositions are generally added to tank reservoirs (typically over top of diluted heel solution or aqueous solution present in the tank reservoirs) according to packaging labels or instructions associated with the adjuvant compositions. Generally, targeted use rates or target concentrations of the adjuvant composition are provided, which depend on various factors such as the formulation of the adjuvant composition, etc. Target use rates or target concentrations may vary widely, which in one embodiment is from about 0.001 lbs/100 gallons to about 50 lb/100 gallons of adjuvant composition to aqueous solution or tank volume, respectively.

In another aspect, the present invention is substantially dry, flowable adjuvant composition comprising, based on 100 parts by weight ("pbw") of the adjuvant composition: (a) from about 25 pbw to about 75 pbw of a polysaccharide; (b) from about 20 pbw to about 60 pbw of a salt composition, wherein an aqueous solution of the adjuvant composition has a pH value of between about 7 and about 10; and (c) from about 20 pbw to about 35 pbw of a dispersing agent. In one embodiment, the dispersing agent is sodium polyacrylate, potassium polyacrylate, a sodium salt of polycarboxylic acid (e.g., Geropon T/36 manufactured by Rhodia Inc.), a surfactant containing sodium 2-[methyloleoylamino]ethane-1-sulphonate (e.g., Geropon T/77 manufactured by Rhodia Inc.) or combinations thereof.

In another embodiment, the substantially dry, flowable adjuvant composition comprises: (a) from about 45 pbw to about 55 pbw of the polysaccharide, wherein the polysaccharide comprises guar gum and/or hydroxypropyl guar; (b) from about 10 pbw to about 20 pbw of diammonium hydrogen phosphate; (c) from about 10 pbw to about 20 pbw of sodium carbonate; and (d) from about 20 pbw to about 30 pbw of the dispersing agent wherein the dispersing agent comprises sodium polyacrylate. In one embodiment, the dispersing agent is capable of acting as a chelating agent as well.

In yet another aspect, the present invention is an aqueous agricultural composition comprising: (a) a water dispersible adjuvant composition, in an amount effective to provide deposition and drift control properties, comprising, based on 100 parts by weight ("pbw") of the adjuvant composition: (i) from about 25 pbw to about 75 pbw of a polysaccharide; and (ii) from about 75 pbw to about 20 pbw of a salt composition, wherein an aqueous solution of the adjuvant solution has a pH value of between about 7 and about 10; and (b) an effective amount of an agricultural active.

In a further aspect, the present invention is a method for treating a target plant, comprising applying to the plant an aqueous solution of an agricultural composition comprising: (a) a water dispersible adjuvant composition, in an amount effective to provide deposition and drift control properties, comprising, based on 100 parts by weight ("pbw") of the adjuvant composition: (i) from about 25 pbw to about 75 pbw of a polysaccharide; and (ii) from about 75 pbw to about 20 pbw of a salt composition, wherein an aqueous solution of the adjuvant composition has a pH value of between about 7 and about 10; and (b) an effective amount of an agricultural active.

In yet a further aspect, the present invention is a method of preparing an aqueous agricultural composition comprising: adding, to a heel solution, a substantially dry, flowable adjuvant composition, in an amount effective to provide deposition and/or drift control properties, comprising, based on 100 parts by weight ("pbw") of the adjuvant composition: (i) from about 25 pbw to about 95 pbw of a polysaccharide—more typically from about 25 pbw to about 75 pbw of a polysaccharide—and (ii) from about 75 pbw to about 5 pbw of a salt composition—more typically from about 75 pbw to about 20 pbw—of a salt composition, wherein an aqueous solution of the adjuvant composition has a pH value of between about 7 and about 10.

In one embodiment, the method further comprises the step of adding an effective amount of an agricultural active to the heel solution, which is typically a glyphosate heel solution, either prior to or after the addition of the substantially dry, flowable adjuvant composition to the heel solution. The salt composition can be diammonium hydrogen phosphate, sodium carbonate or a combination thereof.

In another embodiment, the adjuvant composition further comprises: (iii) from about 20 pbw to about 30 pbw of a dispersing agent, wherein the dispersing agent is sodium polyacrylate, potassium polyacrylate, a sodium salt of polycarboxylic acid, sodium 2-[methyloleoylamino]ethane-1-sulphonate or combinations thereof.

In yet another embodiment, the adjuvant composition further comprises: (iv) from about 20 pbw to about 30 pbw of a chelating agent, wherein the chelating agent is sodium tripolyphosphate, sodium polyacrylate, potassium pyrophosphate, sodium hexametaphosphate or combinations thereof.

DETAILED DESCRIPTION OF INVENTION

As used herein, the term "effective amount" in reference to the relative amount of an agricultural active in an agricultural composition means the relative amount of the active that is effective to control a target, e.g., a target plant, fungus, or insect, when the agricultural composition is applied at a given application rate and for a desired application (e.g., as a herbicide, fungicide, pesticide, etc.).

It has been observed that currently available deposition and drift control adjuvant formulation containing guar gum and/or its derivatives and salts of diammonium sulfate lose compatibility when mixed with low pH agricultural spray solutions such as dilute glyphosate solutions, in particular glyphosate heels, as the amount of guar in the formulation increases.

Generally, agricultural spraying can take place over hundreds of acres with spray solution reservoirs that are hundreds of gallons or more in volume. It is typically impractical and inefficient in commercial applications to entirely clean out these spray solutions from their reservoirs, including lines that feed into these reservoirs, between spray applications. In most cases, small amounts of spray solution remain in the reservoir or feed lines after application(s). This means that residual solutions of previously prepared agricultural compositions/mixtures that are either diluted or non-diluted after the initial application (for example, an aqueous solution of a glyphosate mixture) remain in a tank reservoir after a field application. These residual solutions are called "heels" or "heel solutions."

It is typical to make new spray solutions over top of an existing heel solution instead of completely cleaning out the reservoir and lines. It has been observed that current adjuvant formulations that are added to such heel solutions cannot exceed approximately 25% guar in a dry flowable formulation. Such adjuvant formulations cannot exceed more than about 25% weight by guar because this signifies that a proportionally less amount of diammonium sulfate can be added. (i.e., the ratio of diammonium sulfate to guar cannot exceed about 80:20, respectively, in current commercial formulation without the guar agglomerating, gelling or otherwise not dispersing when mixed into a heel solution.) Such formulations greater than 25% guar typically result in agglomeration or gelling of the guar when added to such heel solutions.

As described above, heel solutions can be present for a number of reasons. If an applicator is spraying a large volume of spray solution per acre being treated, there may be some necessity to re-fill the tank reservoir before depleting the entire spray solution in order to save time, fuel, materials, etc. A heel may also be present if the spray tank is not cleaned completely after each treatment. Heel solutions may also be present if some of the previous utilized spray solution is present in lines or equipment connected to the reservoir. In this case, the main tank may appear clear of the spray solution but heel solutions may remain in the lines and/or equipment.

For example, pesticide labels generally recommend that a spray solution is mixed in the following manner: half the tank is to be filled with water, followed by the addition of adjuvants, actives, antifoams, compatibility enhancing products, and other tank mix additives. The mixture is then further diluted by filling the remaining volume of the tank with water. This process not only allows each product to mix into a fairly dilute solution of the other components, but also aids in mixing the spray solution completely when the second addition of water is made. Pesticide and adjuvant labels can also recommend the order in which the components are mixed to ensure the best compatibility or easiest mixing. On these labels, it is generally recommended that diammonium sulfate, drift control additives, and other adjuvants should be added before the addition of the pesticide. In the case of adding an adjuvant to a heel solution, the recommended order of addition is not possible as there may already be some pesticide in the solution.

Heel solutions reduce the compatibility of adjuvants in the system or the ability of the aduvant to substantially disperse in the system without agglomeration or gelling (hereinafter also referred to as "compatibility"), as seen with mixtures containing hydroxypropyl guar ("HPG"). In one embodiment, compatibility issues surrounding the addition of HPG to a heel solution comes from products containing glyphosate, a systemic non-selective herbicide. Glyphosate is generally formulated as the isopropylamine, potassium or ammonium salt of the parent acid. This salt itself is a weak acid usually having a pH between 4 and 5. These are not optimal conditions for dispersing guar in an aqueous medium. When trying to disperse HPG in dilute solutions of glyphosate or heels, rapid hydration of the solid guar occurs causing a rigid interconnected gel structure to form. This gel can be broken down into smaller aggregates, but they are generally still large enough to cause blockage in the various screens and lines present on an agricultural spray unit. These screens are usually present in both the recirculation system and at points where the liquid passes through the spray nozzles. The spray nozzle screens in particular are especially susceptible to clogging.

It is also understood that aside from heel solutions containing glyphosate, other heel solutions may be associated with the present invention, including but not limited to heel solutions containing 2,4-dichlorophenoxy acetic acid, alpha-[2-(4-chlorophenyl)ethyl]-alpha-(1,1-dimethylethyl)-1H-1,2,4-triazole-1-ethanol or any of the actives referenced in Table 5, herein.

Without being bound by theory, it is believed that the heel problems described above were previously sufficiently addressed by using large amounts of salt (diammonium sulfate) as a physical barrier to rapid hydration, but when a low use rate guar formula is required (which equates to more guar used, e.g., 25% or more guar in the formula proportional to the salt), the physical barrier previously provided by the salt is not sufficient. As used herein, "low use rate" means that a relatively low amount of adjuvant formulation is needed to achieve effective deposition and drift control, as more drift control agent (e.g., polysaccharide) as a percentage of the adjuvant formulation is present. (This, in turn, means that less of the salt is present as a percentage of the adjuvant formulation is present.)

Compositions with decreased amount of salts and increased guar percentages (relative) are desirable for agricultural applications that do not require substantial amounts of diammonium sulfates such as certain fungicide formulations and the like.

To address this problem, the present invention in one embodiment is a substantially dry, flowable adjuvant composition comprising from about 25 pbw to about 95 pbw of a polysaccharide and from about 75 pbw to about 5 pbw of a salt composition (based on 100 parts by weight ("pbw") of the adjuvant composition). Typically, the ratio of the polysaccharide to the salt composition falls within the range of from about 25:55 (polysaccharide:salt composition) pbw to about 55:20 (polysaccharide:salt composition) pbw, and includes ratios that fall in between these ranges (e.g., 30:50 pbw of a polysaccharide to salt composition, respectively).

Suitable polysaccharides include but are not limited to agar, agar derivatives, alginates, alginate derivatives, amylose, amylose derivatives, arabic/acacia gum, arabica/acacia gum derivates, arabinogalactan, arabinogalactan derivatives, benzoin gum, benzoin gum derivatives, carob gum, carob gum derivatives, carrageenan, carrageenan derivatives, cassia gum, cassia gum derivatives, cellulose, cellulose derivatives (including but not limited to methyl cellulose, hydroxylbutyl cellulose, hydroxypropyl cellulose, and mixtures thereof), chitin, chitin derivatives, damar, damar derivatives, dextran, dextran derivatives, dextrin, dextrin derivatives, gellan gum, gelan gum derivatives, gelatin, ghatti gum, ghatti gum derivatives, guar gum, guar gum derivatives, karaya gum, karaya gum derivatives, levan, levan derivatives, locust bean gum, locust bean gum derivatives, pectin, pectin derivatives, pullulan, pullulan derivatives, rhamsan gum, rhamsan gum derivatives, sandarac gum, sandarac gum derivatives, starch, starch derivatives, succinoglucan, succinoglucan derivatives, tamarind gum, tamarind gum derivatives, tara gum, tara gum derivatives, tragacanth gum, tragacanth gum derivatives, xanthan gum, and xanthan gum derivatives.

In one embodiment, the polysaccharide is guar, which can be non-derivatized guar, derivatized guar, cationic guar and/or non-cationic guar. Guar is derived from guar gum, which is the refined endosperm of the legume seed of *Cyamopsis tetragonolobus* (L.) Taub. a plant which physically resembles the soy plant. The gum is a pure food vegetable colloid recognized by the agricultural, chemical and food formulation industry for many years as having excellent thickening, film-forming and stabilizing properties.

Guar solutions or dispersions can be prepared by rapidly sifting dry gum into a vigorously agitated tank of water and permitting the gum to hydrate. Higher water temperatures can shorten the hydration time so long as the heating is not so prolonged or excessive as to degrade the polymer.

Methods of derivatizing guar are well known. For example, the hydroxyl substituents on the guar polymer can undergo reaction via etherification and esterification reactions. In particular, the C-6 hydroxyl position is a reactive position for etherification, e.g., with propylene oxide, but the secondary hydroxyls are also probable sites. U.S. Pat. No. 3,723,408 to Nordgren et al.; U.S. Pat. No. 3,483,121 to Jordan; U.S. Pat. No. 3,740,388 to Montgomery et al. and U.S. Pat. No. 3,723,409 to Yueh describe methods for producing derivatized guars. Typically, guar and derivatives thereof are utilized in the present invention, including but not limited to, hydroxyalkyl guar, for example, hydroxypropyl guar, carboxymethyl guar, hydroxybutyl guar and carboxymethyl hydroxypropyl guar, and mixtures thereof.

Hydroxypropylation increases the gum's solubility, resulting in a product which hydrates rapidly, regardless of water temperature. Both hydroxylalkyl and carboxylmethyl derivatives typically form clearer solutions than standard non-derivatived guar gum and also hydroxyl derivatives resist thermal degradation better than non-derivatived guar. Hydroxypropyl guar gum is particularly useful as a flow modifier and friction reducing agent and is the most preferred derivatived guar gum of this invention.

As used herein, the term "molar substitution" or "(ms)" refers to the number of derivatizing groups per monosaccharide unit of the guar. This is a parameter relating to the derivatizing groups. The molar substitution can be determined by the Zeisel-GC method. The molar substitution utilized by the present invention is typically in the range of from about 0.001 to about 3.

In one embodiment, the derivatized guar has a weight average molecular weight of from 10,000 to 10,000,000 Daltons, more typically, of from about 25,000 to 8,000,000 Daltons and most typically of from about 50,000 to 6,000,000 Daltons.

In one embodiment, the salt composition utilized can comprise one or a combination of basic, neutral and/or acidic salts, more typically a combination of basic and acidic salts, and most typically a combination of basic salts. Comprising part of the substantially dry, flowable adjuvant composition, the effect of the salt combination should be such that the pH of the dry, flowable adjuvant composition in an aqueous solution is greater than about 7. More typically, the pH of an aqueous solution of such adjuvant composition is between about 7 to about 12, and most typically between about 7.5 and about 10.

The basic salts include but are not limited to cations selected from an alkali metal cation, an alkaline earth cation, or a quaternary ammonium cation. Examples include but are not limited to lithium, sodium, potassium, and quaternary ammonium salts of hydroxide, methoxide, ethoxide, isopropoxide, and t-butoxide. More typically the salt composition utilized in the present comprises diammonium hydrogen phosphate, sodium carbonate or a combination thereof. The acidic salts include but are not limited to diammonium sulfate (($NH_4$)$_2SO_4$) and monopotassium phosphate ($KH_2PO_4$). The neutral salts include but are not limited to ammonium nitrate ($NH_3NO_3$) and ammonium phosphate (($NH_4$)$_3PO_4$).

In one embodiment, the dry, flowable adjuvant composition further comprises from about 20 pbw to about 35 pbw of a dispersing agent. In another embodiment, the dry, flowable adjuvant composition further comprises from about 21 to 27 pbw of a dispersing agent. In another embodiment, the dry, flowable adjuvant composition further comprises from about 24 to 26 pbw of a dispersing agent. The dispersing agent can include, but is not limited to: a neutralized polycarboxylic acid, which is typically neutralized homo or copolymers of acrylic acid having a molecular weight of between about 0 to 200,000 Daltons, and in particular sodium polyacrylate; a neutralized polymethacrylic acid; a neutralized polymaleic acid; a neutralized copolymer of diisobutylene-maleic anhydride; a neutralized copolymer of vinylmethyl ether and maleic anhydride; and a neutralized copolymer of styrene-maleic anhydride (wherein counter ions include for example Na and/or K). In one embodiment, the dispersing agent is sodium polyacrylate, potassium polyacrylate, a salt of polycarboxylic acid, or combinations thereof, and, more typically, the dispersing agent is sodium polyacrylate.

In another embodiment, dispersing agent includes but is not limited to: soaps of fatty acids, such as sodium or potassium salts of saturated or unsaturated $C_6$-$C_{24}$ fatty acids, or aminocarboxylic acid derivatives, such as sodium N-lauryl sarcosinate; sulfates and sulfated compounds, such as alkali metal alkyl sulfates of the sodium lauryl sulfate type; polyoxyethyleneated fatty alcohol sulfates; polyoxyethyleneated alkylphenol sulfates an polyoxyethyleneated arylalkylphenol sulfates; phosphoric acid esters of oxyethyleneated compounds, such as polyoxyethyleneated fatty alcohol phosphates; polyoxyethyleneated alkylphenol phosphates and polyoxyethyleneated arylalkylphenol phosphates; alkali metal sulfonates, such as alkylsulfonates, for example alkylsulfoesters of C4-C30 acids of the sodium dialkylsulfosuccinate type; alkylbenzenesulfonates, such as sodium nonylbenzenesulfonate and sodium dodecylbenzenesulfonate; and lignosulfonates; polyoxyethyleneated alkylphenols, such as polyoxyethyleneated nonylphenol an polyoxyethyleneated dodecylphenol; polyoxyethyleneated and/or polyoxypropyleneated fatty acids and fatty alcohols; polyoxyethyleneated and/or polyoxypropyleneated fatty acid alkanolamides; esters of polyhydric alcohols, such as glycerol or propylene glycol esters of fatty acids oils and nutrient fats, mixtures of fatty acids and acetic and/or lactic and/or citric and/or tartaric acid; saccharose esters, such as sugar esters and sugar glycerides; fatty acid esters of sorbitan; and their polyoxyethyleneated and polyoxypropyleneated derivatives, such as polyoxyethyleneated polyethylene glycol or polypropylene glycol esters, polyoxyethyleneated sorbitan esters, polyoxyethyleneated tartaric acid esters and polyoxyethyleneated oleic glycerides.

It is understood that the present invention may further comprise one or more additional components that may be desirable with respect to the particular application or quality/characteristics of the water or solution utilized. Such additional components include but are not limited to water conditioners, chelating or metal binding agents, complexing agents such as ammonium sulfate, buffering agents, such as citric acid, polyacrylic acid, antifoams, spreaders and the like may be used (as necessary or as desired to a particular agricultural application).

In one embodiment, the dry, flowable adjuvant composition further comprises about 5 pbw to about 30 pbw of a chelating agent. In one embodiment, the dry, flowable adjuvant composition further comprises about 21 to 27 pbw of a chelating agent. In one embodiment, the dry, flowable adjuvant composition further comprises about 24 to 26 pbw of a chelating agent. Chelating or metal binding agents include but are not limited to alkyl and aryl derivatives of phosphines, biphosphines, amines, diamines, imines, arsines and hybrids thereof, ethylenediamine tetraacetic acid (EDTA), hydroxyethylethylenediamine triacetic acid (HEDTA), diethylenetriamine pentaacetic acid (DTPA), hydroxyethyliminodiacetic acid (HEIDA), nitrilotriacetic acid (NTA), and their K, Na, NH4 or amine salts, water-soluble aminophosphonates and organic phosphonates type, such as 1-hydroxyethane-1,1-diphosphonates, aminotri(methylenediphosphonate), vinyldiphosphonates, salts of oligomers or polymers of vinylphosphonic or vinyldiphosphonic acid, salts of random cooligomers or copolymers of vinylphosphonic or vinyldiphosphonic acid and of acrylic acid and/or of maleic anhydride and/or of vinylsulfonic acid and/or of acrylamidomethylpropane-sulfonic acid, salts of phosphonated polycarboxylic acids, polyacrylates comprising phosphonate ending(s), salts of cotelomers of vinylphosphonic or vinyldiphosphonic acid and of acrylic acid, and mixtures thereof. Typically, the chelating or metal binding agent is sodium tripolyphosphate, sodium polyacrylate, potassium pyrophosphate, sodium hexametaphosphate or combinations thereof.

In one embodiment, the dispersing agent can perform the functions of a basic salt and a chelating or metal binding agent in addition to its function as a dispersing agent. Typically, a polyacrylate polymer is utilized, and more typically, sodium polyacrylate, which acts as a dispersion agent, a salt and a chelating agent when used in the adjuvant composition of the present invention.

In another embodiment, the adjuvant composition of the present invention comprises: (a) from about 25 pbw to about 55 pbw of hydroxypropyl guar, or from about 35 pbw to about 51 pbw, or from about 48 pbw to about 51 pbw; (b) from about 5 pbw to about 15 pbw of diammonium hydrogen phosphate, or from about 10 pbw to about 12 pbw; (c) from about 5 pbw to about 15 pbw of sodium carbonate, or from about 10 pbw to about 12 pbw; and (d) from about 20 pbw to about 30 pbw of a dispersing agent, or from about 21 to 27 pbw, or from about 24 to 26 pbw. The adjuvant composition can further comprise from about 5 pbw to about 30 pbw of a chelating agent, or from about 21 to 27 pbw, or from about 24 to 26 pbw.

The present invention also comprises agricultural compositions wherein such compositions comprise, in an aqueous solution, an effective amount of an agricultural active and an adjuvant composition.

Suitable agricultural actives are biologically active compounds used to control agricultural pests, insects, fungi, weeds and other undesirable matter. Suitable agricultural actives include but are not limited to pesticides, herbicides, plant growth regulators, crop dessicants, fungicides, bactericides, bacteriostats, insecticides, miticides, nematocides, and insect repellants. Agricultural compositions are compositions that include such agricultural actives.

Suitable herbicides include but are not limited to triazine herbicides such as metribuzin, hexaxinone, or atrazine; sulfonylurea herbicides such as chlorsulfuron; uracils such as lenacil, bromacil, or terbacil; urea herbicides such as linuron, diuron, siduron, or neburon; acetanilide herbicides such as alachlor, or metolachlor; thiocarbamate herbicides such as benthiocarb, triallate; oxadiazolone herbicides such as oxadiazon; phenoxyacetic acids such as 2,4-D; diphenyl ether herbicides such as fluazifop, acifluorfen, bifenox, or oxyfluorfen; dinitro aniline herbicides such as trifluralin; organophosphonate herbicides such as glyphosate salts and esters; dihalobenzonitrile herbicides such as bromoxynil, or ioxynil, dipyridilium herbicides such as paraquat.

Suitable fungicides include but are not limited to nitrilo oxime fungicides such as cymoxanil; imidazole fungicides such as benomyl, carbendazim, or thiophanate-methyl; triazole fungicides such as triadimefon; sulfenamide fungicides, such as captan; dithio-carbamate fungicides such as maneb, mancozeb, or thiram; chloronated aromatic fungicides such as chloroneb; dichloro aniline fungicides such as iprodione, strobilurin fungicides such as kresoxim-methyl, trifloxystrobin or azoxystrobin; chlorothalonil; copper salt fungicides such as copper oxychloride; sulfur; phenylamides; and acylamino fungicides such as metalaxyl or mefenoxam.

Suitable insecticides include but are not limited to carbamate insecticides, such as methomyl, carbaryl, carbofuran, or aldicarb; organo thiophosphate insecticides such as EPN, isofenphos, isoxathion, chlorpyrifos, or chlormephos; organophosphate insecticides such as terbufos, monocrotophos, or terachlorvinphos; perchlorinated organic insecticides such as methoxychlor; synthetic pyrethroid insecticides such as fenvalerate, abamectin or emamectin benzoate, neonicotinoide insecticides such as thiamethoxam or imidacloprid; pyrethroid insecticides such as lambda-cyhalothrin, cypermethrin or bifenthrin, and oxadiazine insecticides such as indoxacarb, imidaclopryd, or fipronil.

Suitable miticides include but are not limited to propynyl sulfite miticides such as propargite; triazapentadiene miticides such as amitraz; chlorinated aromatic miticides such as chlorobenzilate, or tetradifan; and dinitrophenol miticides such as binapacryl. Suitable nematicides include carbamate nematicides, such as oxamyl.

Pesticide compounds are, in general, referred herein to by the names assigned by the International Organization for Standardization (ISO). ISO common names may be cross-referenced to International Union of Pure and Applied Chemistry ("IUPAC") and Chemical Abstracts Service ("CAS") names through a number of sources such as, for example, the *Compendium of pesticide Common Names*.

In one embodiment, the agricultural active is selected from glufosinate, glyphosate, water soluble glufosinate salts, water soluble glyphosate salts, and mixtures thereof, including, for example sodium, potassium, isopropyl amine, or ammonium salts.

The present invention has been found to be particularly effective in its mixing or addition into a heel solution, typically a glyphosate heel solution. In one embodiment, an aqueous agricultural composition is prepared by adding, to an already existing heel solution, an effective amount of a water dispersible adjuvant composition (based on 100 pbw of the adjuvant composition): (i) from about 25 pbw to about 75 pbw of a polysaccharide, and (ii) from about 75 pbw to about 20 pbw of a salt composition at a predetermined target concentration having a pH value of between about 7 and about 12 in solution. The adjuvant composition can optionally include from about 20 pbw to about 30 pbw of a dispersing agent as disclosed herein. The adjuvant composition can optionally include from about 5 pbw to about 30 pbw of a chelating agent as disclosed herein.

The agricultural compositions of the present invention may, optionally, further comprise one or more agronomically acceptable solvent. Suitable solvents include, for example, water, and organic solvents, such as for example, alkylated aromatic solvents, such as toluene or alkylated naphthalenes and mineral oil fractions, such as paraffinic hydrocarbons, vegetable oils, alkylated seed oils, dibasic esters. Typically, water is utilized to dilute the agricultural composition or heel solution, which can include deionized water, hard water (i.e., containing various polyvalent metal cations, such as barium, calcium, magnesium, other minerals or a combination thereof), tap water and the like. Such agricultural solutions are generally utilized in spray solutions.

Currently available adjuvant formulations containing guar do not appear to be compatible with glyphosate heel solutions at guar concentrations above about 25%. Referring to Table 1 (a), for example, it is illustrated that heel solutions are not compatible with guar concentrations higher than about 20 wt % or 25 wt % relative to the wt % of diammonium sulfate. Current commercially-available formulations do not exceed 25 wt % guar (relative to wt % of diammonium sulfate salt).

In one embodiment, low use rate means where the adjuvant composition of the present invention is added to an aqueous tank mixture at less than about 8 lbs/100 gallon. In another embodiment, low use rate means where the adjuvant composition of the present invention is added to an aqueous tank mixture at less than about 6 lbs/100 gallons, more typically less than 4 lbs/100 gallons. In another embodiment, low use rate means where the adjuvant composition of the present invention is added to a tank mixture at less than about 4 lbs/100 gallons. In another embodiment, low use rate means where the adjuvant composition of the present invention is added to a tank mixture at less than about 3 lbs/100 gallons. In another embodiment, low use rate means where the adjuvant composition of the present invention is added to a tank mixture at less than about 2.5 lbs/100 gallons. In a further embodiment, low use rate means where the adjuvant composition of the present invention is added to a tank mixture at less than about 2 lbs/100 gallons. In yet a further embodiment, low use rate means where the adjuvant composition of the present invention is added to a tank mixture at less than about 1 lbs/100 gallons. In still a further embodiment, low use rate means where the adjuvant composition of the present invention is added to a tank mixture at less than about 0.6 lbs/100 gallons.

Currently in the art there is disclosed adjuvant compositions having from 87.50 to 99.80 wt % diammonium sulfate salts directed to uniformly distribute and hydrate guar gum in an aqueous medium. Without being bound by theory, it is believed that large amounts of water soluble fertilizers such as the diammonium sulfate salts offers dilution effects which build up a physical barrier to separate guar gum particles. It is believed that through this process large amounts of crystal salts provide at least two effects: (1) ensures a maximum surface area of guar gum exposed in aqueous medium and (2) enhances the hydration of guar gum. However, by increasing the guar gum as a percentage of the adjuvant formulation, (which necessarily means a lower amount of diammonium sulfate as a percentage of the adjuvant formulation and at a lower proportional ratio to the guar gum) a smaller amount of crystal salts of diammonium sulfate (AMS) is present to provide the aforementioned effects. Without being bound by theory, it is believed that this lower relative amount of diammonium salt is insufficient to properly and efficiently hydrate the guar gum into the bulk medium. Therefore, the formulations or present invention that contains an increased percentage of guar and, consequently, a proportionally decreased amount of salt address these problems associated with the prior art.

The uniform distribution and hydration of 50 wt % hydroxypropyl guar ("HPG") with 50 wt % salt mixtures were observed as follows. With at least 50 wt % HPG, the formulations tend to initially spread on the air water interface, then gradually disperse to bulk aqueous medium, and eventually hydrate in the bulk aqueous solution. Suitable buffers and suitable dispersing agents can be utilized for preparing such mixtures. The conditions affecting guar gum hydration in glyphosate heel solutions have been studied. Several types of salts, such as acidic salts, basic salts and neutral salts, have been tested in combination with 50 wt % HPG. The compatibility test results with HPG combined with salt compositions having an overall basic pH value illustrated that the such formulation is capable of preventing rapid gellation and agglomeration of HPG in aqueous glyphosate heel solutions.

Experiments

TABLE 1

The compatibility test of HPG combinations with ammonium sulfate

| Ammonium Sulfate:HPG | Heel (Buccaneer) | No Heel (Buccaneer) |
|---|---|---|
| 95:5 | Compatible | Compatible |
| 85:15 | Compatible | Compatible |
| 80:20 | Compatible | Compatible |
| 75:25 | Not Compatible | Compatible |
| 50:50 | Not Compatible | Compatible |

As referenced above, it has been observed that formulations cannot exceed approximately 20% or 25% guar in a dry flowable formulation added to glyphosate heel solutions. With such formulations, the guar does not properly disperse into the solution.

TABLE 2

The compatibility test of AgRHO DEP 3000 (hydroxypropyl guar, HPG) combination with salt mixtures

| AgRHO DEP 3000:$(NH_4)_2HPO_4$:$Na_2CO_3$:$(NH_4)_2SO_4$ | Heel (Buccaneer) | No Heel (Buccaneer) |
|---|---|---|
| 30:50:10:10 | Compatible | Compatible |

Referring to Table 2, it is observed that a combination of basic and acidic salts, which provides an overall basic pH value, is utilized. In other words, the salt combinations with overall basic pH values, not necessary limited at basic salt combinations, is believed to assist in uniform hydration of HPG in aqueous medium. Various tradenames for HPG are used herein and include AgRHO DEP 3000 and AgRHO DR 2000, which have a ms in the range of between about 0.001 to about 3, more typically, between about 0.001 to about 2, and most typically, between about 0.001 to about 1.5.

Referring now to Table 3, examples of formulations of the present invention were prepared by grinding guar gum and salts together by a mortar and pestle. For the compatibility test, HPG and salt mixtures were tested with and without heels (~25% heel) under D.I. water and hard water (~300 ppm total hardness measured as $MgCO_3$ and $CaCO_3$). With heel test, 100 mL of water (D.I. water or medium hardness water) was added into a 400 mL beaker followed by the addition of 1.5 g of glyphosate (Buccaneer® manufactured by Tenkoz Inc., Alpharetta, Ga.) (~1.5% wt/wt). The solution was gently mixed by spatula. Formulation is added into the aqueous solution to achieve the target polymer concentration. The solution was gently mixed by spatula until uniform. Another 4.5 g glyphosate is added into solution followed by the addition of 100 mL water. The final glyphosate concentration in solution was ~3 wt %. Without heel test, 100 mL of water (D.I. water or hard water) was added into a 400 mL beaker followed by the addition of adjuvant. The solution was gently mixed by spatula until uniform. Upon the addition of 6 g glyphosate, the solution was gently mixed by spatula until uniform. Another 100 mL is added into the solution and the final glyphosate concentration in solution was ~3 wt %. The solutions were then allowed to fully hydrate for 10+ minutes before being poured through an 80-100 mesh sieve (180-150 micron) to ensure that no gellation or agglomeration has occurred. This size was selected based on the relative screen sizes found in agricultural spray filters and nozzles.

For the compatibilities with fungicide and insecticide, the formulations were tested with and without heels (~25% heel) under D.I. water. With heel test, 100 mL of water was added into a 400 mL beaker followed by the addition of active ingredients (~25% of their final use rates). The solution was gently mixed by spatula. Formulation is added into the aqueous solution to achieve the target polymer concentration. The solution was gently mixed by spatula until uniform. More active ingredients were added into solution followed by the addition of 100 mL water. The final active concentrations in solution were close to their normal use rates. Without heel test, 100 mL of water was added into a 400 mL beaker followed by the addition of adjuvant. The solution was gently mixed by spatula until uniform. Upon the addition of active ingredients, the solution was gently mixed by spatula until uniform. Another 100 mL was added into the solution and the final active concentrations in solution were close to their normal use rates. The solutions were then allowed to fully hydrate for 10+ minutes before being poured through an 80-100 mesh sieve (180-150 micron) to ensure that no gellation or agglomeration has occurred.

Several types of salts, such as acidic salts, basic salts and neutral salts, have been tested in combination with 50 wt % HPG. Formulations prepared by HPG with 50 wt % salts, such as acidic salts: diammonium sulfate ($(NH_4)_2SO_4$), Citric Acid ($C_6H_8O_7$), and monopotassium phosphate ($KH_2PO_4$), neutral salts: ammonium nitrate ($NH_3NO_3$) and ammonium phosphate ($(NH_4)_3PO_4$), and basic salts: diammonium hydrogen phosphate ($(NH_4)_2HPO_4$) and sodium carbonate ($Na_2CO_3$), were tested for compatibility with a glyphosate heel and without a glyphosate heel in D.I. water. Tests performed in glyphosate heel solutions, showed that basic salts provided the best effect for preventing rapid gellation and agglomeration of HPG. In tests performed without glyphosate heel solutions, the basic salt, $(NH_4)_2HPO_4$, showed improved compatibility. In addition, the overall effects of salts on preventing gelling and agglomeration problems were ranked as the following (from least to greatest effect on compatibility). With heel test: $NH_3NO_3$~$(NH_4)_3PO_4$<$(NH_4)_2SO_4$~$KH_2PO_4$<$(NH_4)_2HPO_4$<$Na_2CO_3$. Without heel test: $NH_3NO_3$~$(NH_4)_3PO_4$<$Na_2CO_3$<$(NH_4)_2SO_4$~$KH_2PO_4$<$(NH_4)_2HPO_4$.

Based on the compatibility results of various salts, tests were conducted to determine the feasibility of using basic salt mixtures as buffers for guar gum (i.e., separating each other and hydrating in aqueous medium). Formula with 50 wt % HPG and various ratios of $(NH_4)_2HPO_4/Na_2CO_3$ mixtures were prepared for the compatibility tests with/without glyphosate heel solutions. In addition, the overall hydration rates of HPG in D.I. water and hard water were evaluated as the final formulations would be mainly used for insecticides and fungicides applications. The overall results were shown in Table 3, with ratios in terms of weight.

not contain any metal binding agents. But in terms of hydrations, HPG was able to hydrate without any gelling and agglomeration problems in the conditions described above.

Referring now to Table 4, a chelating agent, such as sodium polyacrylate, was added in the formulations to prevent the formation of insoluble salts with hard water (~300ppm). The formulation of HPG:sodium polyacrylate $(CH_2$—$CH$ $(COONa)$—$):(NH_4)_2HPO_4:Na_2CO_3$ at a ratio of 50:25:12.5: 12.5, respectively, provided uniform dispersion of HPG and providing a suitable hydration environment for HPG in aque-

TABLE 3

The compatibility test of HPG combinations with salt mixtures

| Ratios of HPG:$(NH_4)_2HPO_4$:$Na_2CO_3$ | Heel (Buccaneer) | No Heel (Buccaneer) | DI-Water (alone) | Hard water (~310 ppm) |
| --- | --- | --- | --- | --- |
| 50:0:50 | Compatible | Not Compatible | pH ~10.8 Did Not Hydrate | Form Insoluble Salts |
| 50:12.5:37.5 | Compatible | Not Compatible | pH ~10.4 Did Not Hydrate | Form Insoluble Salts |
| 50:25:25 | Compatible | Compatible | pH ~9.3 Hydrate | Form Insoluble Salts |
| 50:35:15 | Compatible | Compatible | pH ~8.9 Hydrate | Form Insoluble Salts |
| 50:37.5:12.5 | Compatible | Compatible | pH ~8.7 Hydrate | Form Insoluble Salts |
| 50:40:10 | Compatible | Compatible | pH ~8.5 Hydrate | Form Insoluble Salts |
| 50:45:5 | Compatible | Compatible | pH ~8.3 Hydrate | Form Insoluble Salts |
| 50:50:0 | Not Compatible | Compatible | pH ~8.0 Hydrate | Form Insoluble Salts |

Formulations of HPG:$(NH_4)_2HPO_4$:$Na_2CO_3$ in weight ratios of 50:25:25, 50:35:15, 50:37.5:12.5, 50:40:10, and 50:45:5 showed desired compatibility effects under experiment conditions. In addition, the formulations tend to form insoluble salts with hard water ions in hard water (~300 ppm total hardness measured as $MgCO_3$ and $CaCO_3$) as they do ous solution. In the presence of sodium polyacrylate, this formula did not form insoluble salts with hard water. In addition, sodium polyacrylate also acted as a basic salt buffer and a dispersing agent in the formula. Referring to Table 5, this formula also showed good compatibility with herbicides, insecticides and fungicides.

TABLE 4

The compatibility test of HPG combinations with salt mixtures
Table 4 The compatibility test of HPG combinations with salt mixtures

| Formula | Heel (Buccaneer) | No Heel (Buccaneer) | Hard Water (~310 ppm) |
| --- | --- | --- | --- |
| AgRHO DEP 3000:Sodium polyacrylate:$(NH_4)_2HPO_4$:$Na_2CO_3$ 50:25:12.5:12.5 | Compatible | Compatible | Ok hydration pH ~8.6 |
| AgRHO DR 2000:Sodium polyacrylate:$(NH_4)_2HPO_4$:$Na_2CO_3$ 50:25:12.5:12.5 | Compatible | Compatible | Ok hydration pH ~8.4 |
| Underivatized Guar:Sodium polyacrylate:$(NH_4)_2HPO_4$:$Na_2CO_3$ 50:25:12.5:12.5 | Compatible | Compatible | Ok hydration pH ~8.6 |

TABLE 5

| Compatibility tests with insecticides and fungicides | | |
|---|---|---|
| HPG:—$CH_2$—CH(COONa)—:$(NH_4)_2HPO_4$:$Na_2CO_3$ 50:25:12.5:12.5 | Heel | No Heel |
| Roundup WeatherMax (Herbicide, e.g., Glyphosate [potassium salts]) | Compatible* | Compatible* |
| Tenkoz Amine 4 (Herbicide, e.g., 2,4 D [DMA salts]) | Compatible | Compatible |
| Folicur 3.6 (Fungicide, e.g., Tebucoazole) | Needs continuous mixing | Needs continuous mixing |
| Headline (Fungicide, e.g., Pyraclostrobin) | Compatible | Compatible |
| Quilt (Fungicide, e.g., Azoxystrobin) | Compatible | Compatible |
| Rugby 10 ME (Insecticide, e.g., Cadusafos) | Compatible | Compatible |
| Warrior with Zeon Technology (Insecticide, e.g., Lambda-cyhalothrin) | Compatible | Compatible |
| Proaxis (Insecticide, e.g., Gamma-cyhalothrin) | Compatible | Compatible |

*The solution became hazy, however, no gel formation was observed when pouring solution through the 80-mesh screen. In addition, sample solution went clear after addition of water conditioning agents.

From experiments, the formula of about 50 wt % HPG mixing with about 25 wt % sodium polyacrylate, about 12.5 wt % diammonium hydrogen phosphate, and about 12.5 wt % sodium carbonate has been identified as one optimal formula for ensuring uniform distribution of HPG (and a maximum surface area of HPG in aqueous solution). The 25 wt % sodium polyacrylate also appears to have multiple beneficial effects: as water conditioning agent, a basic salt for separating and preventing rapid guar hydration at the air/water (a/w) interface, and as a dispersing agent. It is believed that the 12.5 wt % diammonium hydrogen phosphate and 12.5 wt % sodium carbonate mixtures act as basic buffers to separate guar gum particles and avoid hydration leading to agglomeration or gelling. The formula of the present invention contains up to 50 wt % HPG, and offers compatibility with aqueous glyphosate heel solutions. In addition, the formula is also compatible with insecticides and fungicides. Many other formulations with various salts combinations and the additions of spreading agents and metal binding agents can be also utilized.

It should be apparent that embodiments other than those expressly discussed above come within the spirit and scope of the present invention. Thus, the present invention is not limited by the above description but is defined by the appended claims.

What is claimed is:

1. A flowable adjuvant composition for drift control comprising, based on 100 parts by weight ("pbw") of the adjuvant composition:

(a) from about 25 pbw to about 95 pbw of a hydroxypropyl guar; and (b) from about 75 pbw to about 5 pbw of a salt composition consisting of diammonium hydrogen phosphate and sodium carbonate in a weight ratio of 1:1 to 9:1, whereby the adjuvant composition is capable of hydrating in a heel solution remaining in a tank reservoir after a field application.

2. The adjuvant composition of claim 1 wherein the hydroxypropyl guar has a weight average molecular weight of from about 50,000 to about 30,000,000 Daltons.

3. The adjuvant composition of claim 2 wherein the hydroxypropyl guar has a weight average molecular weight of from about 1,000,000 to about 6,000,000 Daltons.

4. The adjuvant composition of claim 1 wherein an aqueous solution of the adjuvant composition has a pH value of between about 7 and about 10.

5. The adjuvant composition of claim 1 wherein 25 to 55 pbw of the hydroxypropyl guar, (a), are present.

6. The adjuvant composition of claim 1 wherein the ratio of the polysaccharide to the salt composition is within the range of 25:55 to 55:20.

7. The adjuvant composition of claim 1 wherein the ratio of the polysaccharide to the salt composition is 30:50 pbw.

8. The adjuvant composition of claim 1 comprising 45 to 55 pbw polysaccharide comprising hydroxypropyl guar, 10 to 20 pbw diammonium hydrogen phosphate, 10 to 20 pbw sodium carbonate, and 20 to 30 pbw dispersing agent comprising sodium polyacrylate.

* * * * *